(12) United States Patent
Søgaard-Andersen

(10) Patent No.: US 7,413,569 B2
(45) Date of Patent: Aug. 19, 2008

(54) IMPLANT

(75) Inventor: Torben Søgaard-Andersen, Draguignan (FR)

(73) Assignee: Nortec Medical Development S.A., Luxembourg (LU)

(*) Notice: Subject to any disclaimer, the term of this patent is extended or adjusted under 35 U.S.C. 154(b) by 309 days.

(21) Appl. No.: 10/537,713

(22) PCT Filed: Jul. 21, 2003

(86) PCT No.: PCT/IL03/02889

§ 371 (c)(1),
(2), (4) Date: Jun. 3, 2005

(87) PCT Pub. No.: WO2004/010897

PCT Pub. Date: Feb. 5, 2004

(65) Prior Publication Data

US 2006/0235543 A1   Oct. 19, 2006

(30) Foreign Application Priority Data

Jul. 25, 2002   (DK) .................... PA 2002 01137
Sep. 18, 2002   (DK) .................... PA 2002 01376

(51) Int. Cl.
  A61B 17/08   (2006.01)
  A61F 2/02    (2006.01)
(52) U.S. Cl. ..................... 606/151; 623/23.72
(58) Field of Classification Search ... 623/23.64–23.74; 606/151

See application file for complete search history.

(56) References Cited

U.S. PATENT DOCUMENTS

| 5,098,397 | A |   | 3/1992 | Svensson et al. ............ 604/175 |
| 5,098,398 | A |   | 3/1992 | Lundgren .................... 604/175 |
| 6,017,355 | A |   | 1/2000 | Hessel et al. ................ 606/184 |
| 6,254,642 | B1 | * | 7/2001 | Taylor ...................... 623/23.64 |
| 6,669,735 | B1 | * | 12/2003 | Pelissier .................. 623/23.74 |
| 6,726,660 | B2 | * | 4/2004 | Hessel et al. ................ 604/175 |
| 6,783,554 | B2 | * | 8/2004 | Amara et al. ............ 623/23.76 |
| 7,083,648 | B2 | * | 8/2006 | Yu et al. .................. 623/15.11 |
| 2002/0099344 | A1 |   | 7/2002 | Hessel et al. ................ 604/338 |

FOREIGN PATENT DOCUMENTS

| DK | PA 200000521 | * | 3/2000 | ................ 604/175 |
| WO | WO 87/06122 |   | 10/1987 | |
| WO | WO 01/08597 |   | 2/2001 | |

* cited by examiner

Primary Examiner—Suzette J Gherbi
(74) Attorney, Agent, or Firm—Winston & Strawn LLP

(57) ABSTRACT

An implant serving for surrounding e.g. an intestine on hypodermal implantation in an animal or a human body. The implant includes an outer ring, an inner ring arranged in the outer ring about a joint axis, and a number of anchoring links extending between the outer ring and the inner ring. The inner ring, outer ring and two successive connecting links define an opening in which an anchoring means is secured. The free end of the anchoring means is anchored in fascia. The preferred application for the implant is prophylactic and therapeutic treatment of a hernia, especially a hernia originating from an enterostomy.

17 Claims, 5 Drawing Sheets

IMPLANT

Figure 1:
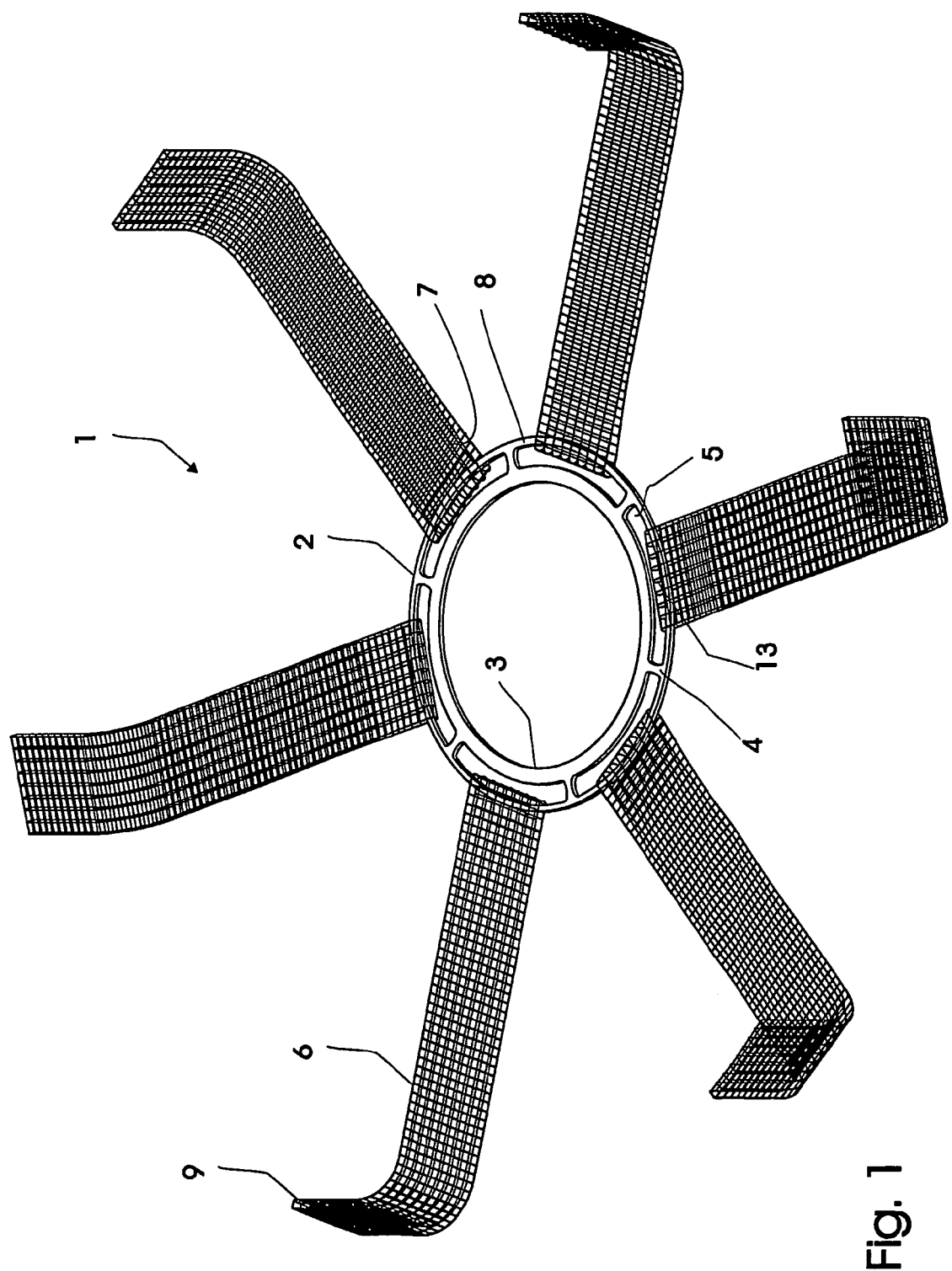

The invention relates to a hypodermal implant for surrounding for example an intestine on implantation into an animal or a human body.

Surgical intervention via the wall of the abdominal cavity causes weakened areas in the musculature of the abdominal cavity and thereby increased risk of hernia formation.

Such weakened areas form hernial orifices. Via these orifices abdominal organs, such as intestinal tissue and/or mesentery, or parts of these organs can be pressed into so-called hernia sacs and be isolated in these to a greater or smaller extent.

In many cases such a hernia does not cause the patient any inconvenience but as the hernia sac and its content are joined, the hernia becomes irreducible and can be felt and seen in practically all positions that the body might assume. To this should be added that the hernial orifice gradually becomes tight, and the blood supply to the hernia is affected. This can result in volvulus and much and severe pain in the stomach. There is furthermore a risk of infection, gangrene, intestinal perforation, shock and even death.

Hernia formations in connection with an established enterostomy are therefore not wanted. Such a hernia is typically provoked by physical exertions, such as lifting or coughing, or can even, especially immediately after the surgical intervention, be provoked by more or less violent peristaltic movements or mass movements.

During these physical exertions or movements the intestine and parts of the surrounding tissue respectively will be pressed in towards the hernia orifices at the risk of formation of a hernia in the area at the newly established stoma. For example a bulging hernia will be a great nuisance when a stoma pouch is to be kept adhered across the stoma as the adherend of a stoma pouch often is not flexible enough to follow the hernia bulge and will therefore loose its adhesive hold on the skin. To this should be added that a hernia can provoke defecation obstructing or—blocking constrictions in the intestine.

A first aspect of the present invention is to provide a hypodermal, biocompatible implant of the kind mentioned in the opening paragraph that has a simple, inexpensive design and easily can be implanted.

A second aspect of the present invention is to provide a hypodermal implant that cannot be felt by a patient having the implant implanted.

The novel and unique feature according to the invention, whereby this is achieved, is the fact that the implant comprises an outer ring, an inner ring arranged in the outer ring about a joint axis, and a number of connecting links extending between the outer ring and the inner ring.

The outer and inner rings can preferably be concentrically arranged about their joint axis, the connecting links connecting the two rings at a radial distance from each other.

An implant designed in such a way will appear as a mainly flat ring that will not take up much space in the area of e.g. the abdominal cavity, into which it is implanted, and will therefore not be felt by the patient.

Preferably the implant is designed with thin rings having a small wall thickness, for example between 0.5 and 5 mm so that the rings can yield in a controlled manner according to the peristaltic movements of the intestine in the area in which the inner ring is surrounding this intestine.

The connecting links, which for example can be comprised of at least one rod or thread, can advantageously be distributed along the ring with a mutual angular distance so that they jointly form a number of openings between the inner ring and the outer ring. The surgeon can advantageously use these openings during implantation for securing the implant to a tissue structure.

At least one elongated anchoring means extending outwards from the opening or inner ring to a free end can furthermore be mounted in the openings. The anchoring means serve for anchoring the implant and secure it on the prefixed implantation site.

Both the implant and the anchoring means can expediently be made of a biocompatible material to ensure that the implant will not provoke irritation or inflammation at the risk of rejection. The material chosen for the anchoring means must furthermore be flexible so that the anchoring means easily can be directed in direction towards their anchoring site.

If the implant is made of a flexible material, for example a material having memory, the surgeon will easily be able to press the implant together with for example a Pean so that the implant can be kept folded and can be introduced through the abdominal wall through an incision smaller than the diameter of the implant. When the grip of the Pean is released, the implant will unfold again to be placed to surround for example an intestine.

The implant can effectively retain and guide the intestine in an area of the abdominal cavity where there is a risk of hernia formations to prevent such hernia formations. The flexibility of the implant furthermore means that the patient cannot feel it in its implanted state.

Anchoring means in form of e.g. PROLENE meshes are for example known from the inventor's own international patent application WO 01/08597. The length of the anchoring means can be adapted to the actual anatomic conditions, and the free end can in a simple way be secured in the adjacent fascia with for example knot sutures or staples. The meshes can be made of any biocompatible, flexible material known in the art. Preferred materials are those that conventionally are used in the art for hernia treatment.

In a preferred embodiment of the implant according to the invention the anchoring means are embedded in or otherwise integrated in at least the outer ring. This embodiment is especially inexpensive and quick to manufacture as the entire implant including the anchoring means can be made in one and the same processing step, for example at moulding or cutting from a larger workpiece.

A section of the intestine that e.g. is to be taken through an abdominal incision to construct a stoma is first taken through the inner ring of the implant. The implant is positioned at subcutis where it is secured by means of e.g. a number of knot sutures in the openings. Subsequently the free ends of the anchoring means are secured to fascia by means of e.g. staples or knot sutures.

As the anchoring means are either secured in an opening along the outer ring, embedded in either the outer ring or an integrated part of both the inner ring and the outer ring, friction between the surface of the anchoring means and the area of the intestine passing through and in contact with the inner ring can advantageously be avoided. Such a friction can for example be generated by the peristaltic movements of the intestine or mass movements, and repeated friction would at worst result in the injury of the intestine and its content seeping into and infecting the abdominal cavity.

An anchoring means can alternatively be distanced from the implant and thereby the intestine by means of at least one thread secured in an opening in the implant and connected to the anchoring means at the anchoring end of this means. A thread preferably made of a biocompatible material can possibly be impregnated in a known way with an antimicrobial preparation such as AgNO₃ or an antibiotic to reduce the infection risk during and after implantation.

The thickness of the ring walls and the diameter of the rings can be the same or not and will typically depend on the specific application. Correspondingly the anchoring means can be provided with different lengths.

Figure 2:
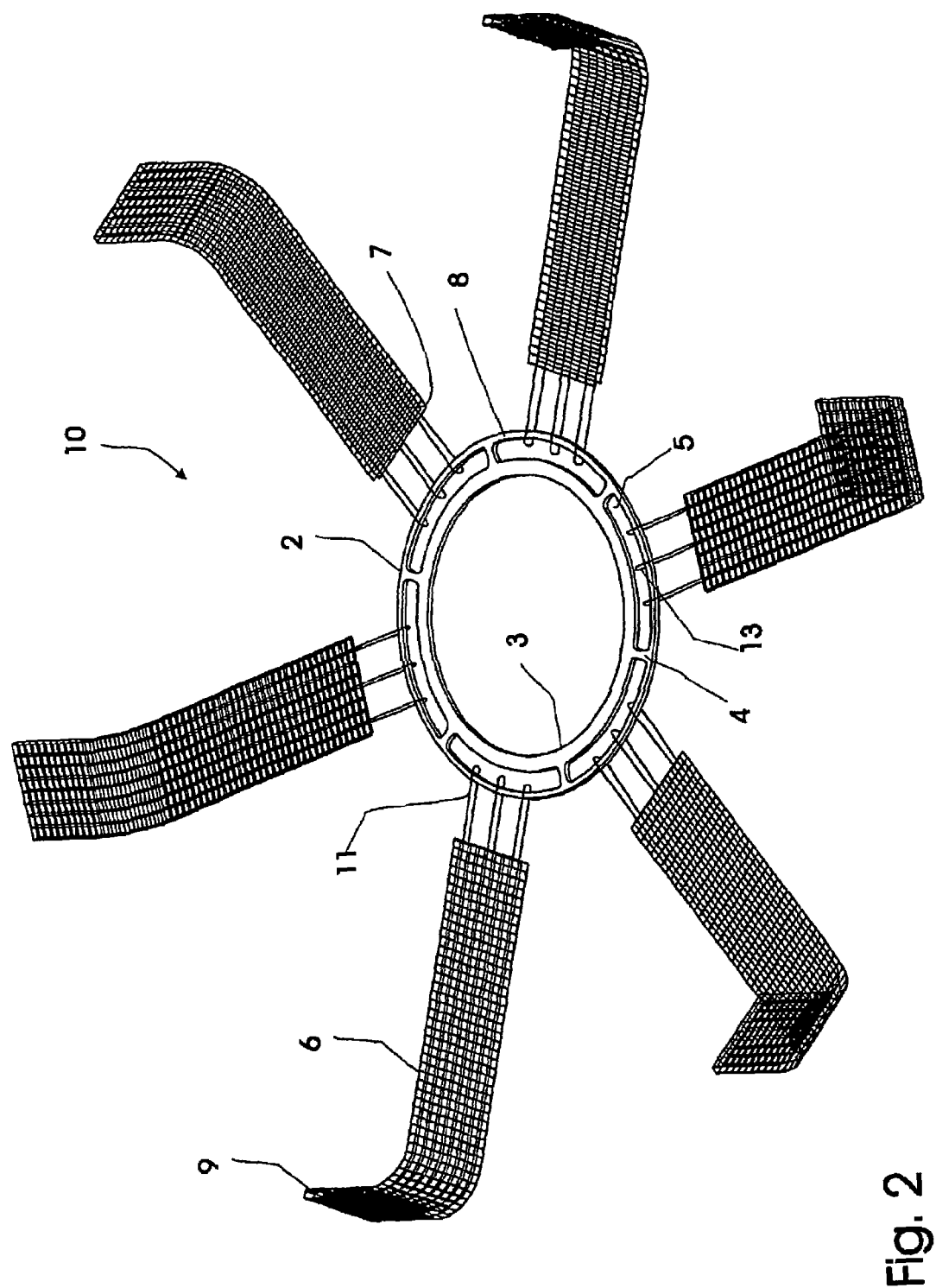
Figure 3:
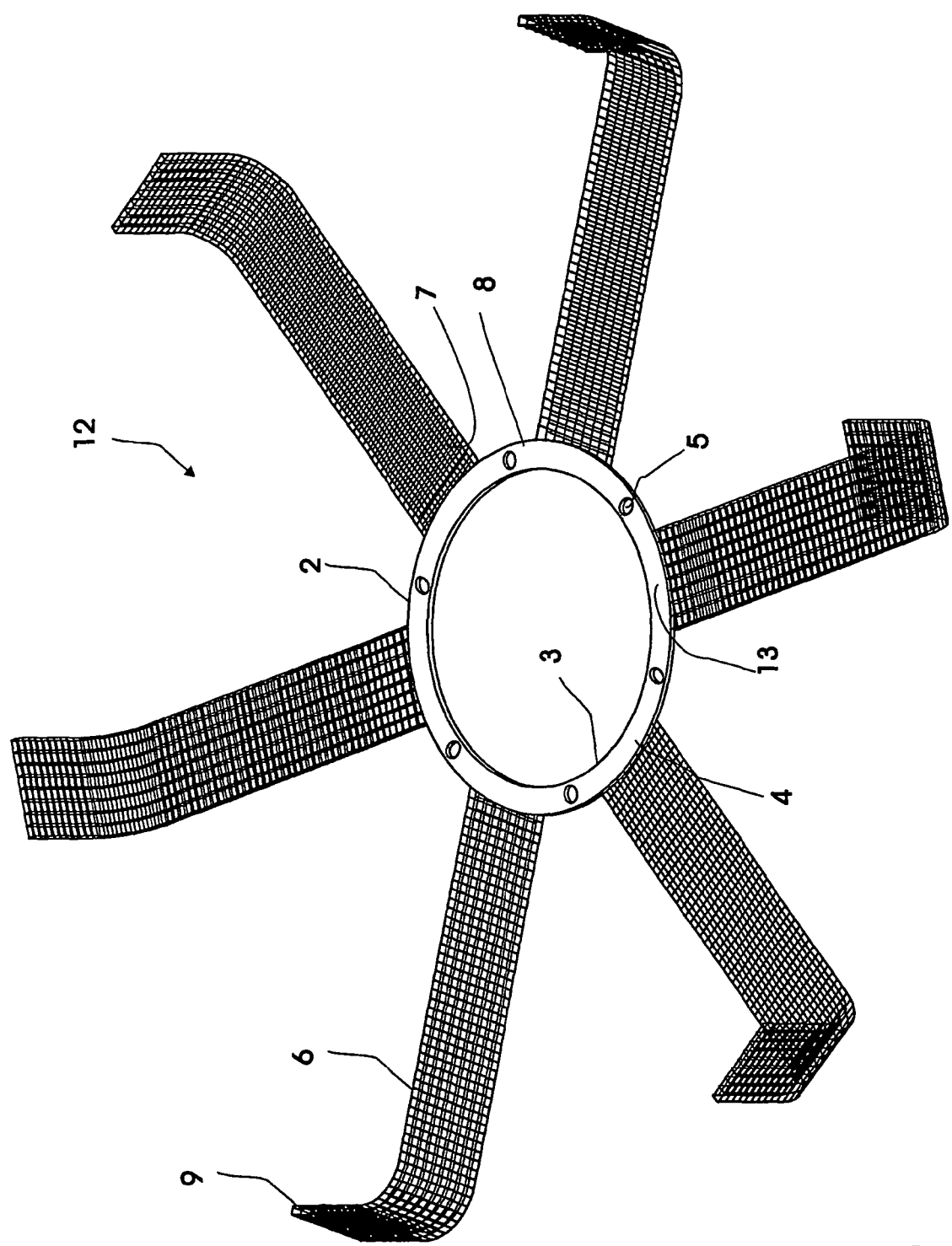
Figure 4:
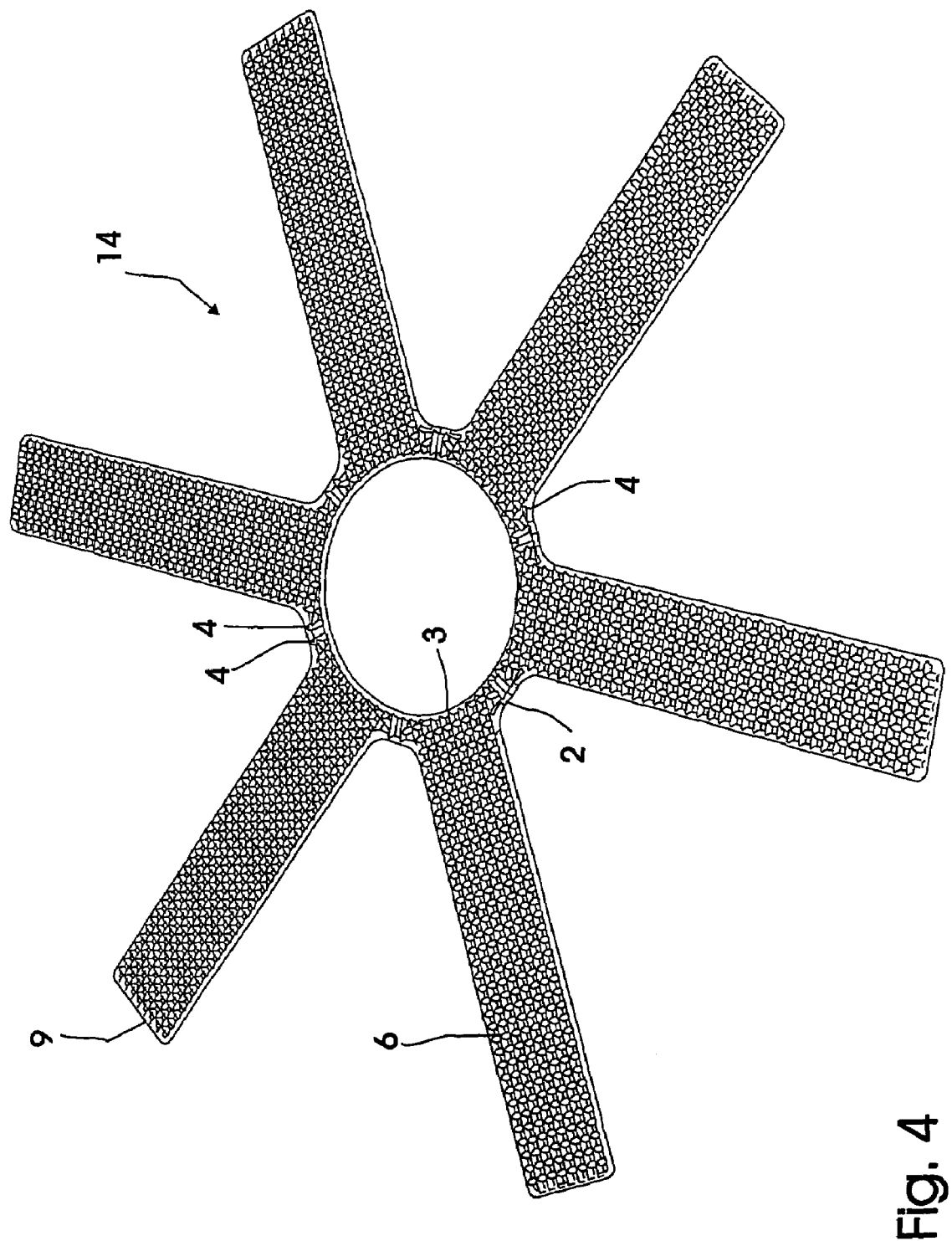
Figure 5:
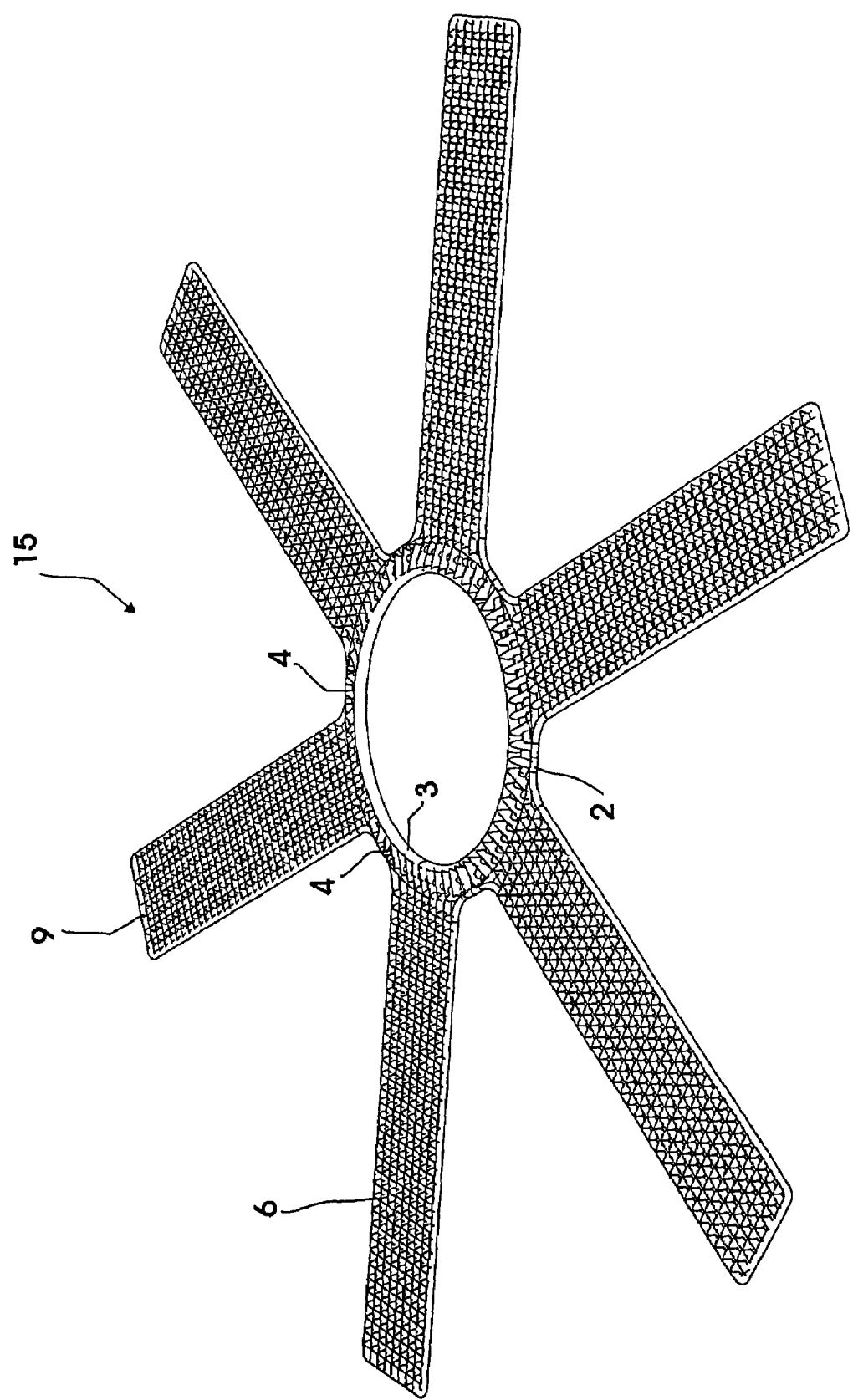

The invention will be explained in greater details below, describing only exemplary embodiments with reference to the drawing, in which FIG. 1 is a perspective view of a first embodiment of an implant according to the invention, FIG. 2 is a perspective view of a second embodiment of an implant according to the invention, FIG. 3 is a perspective view of a third embodiment of an implant according to the invention, FIG. 4 is a perspective view of a fourth embodiment of an implant according to the invention, and FIG. 5 is a perspective view of a fifth embodiment of an implant according to the invention, Below the invention is described on the assumption that the implant is used for a person who has gone through a stoma operation and that the anchoring means are biocompatible meshes.

FIG. 1 is a perspective view of a hypodermal implant 1 according to the invention.

The implant 1 has an outer ring 2 and an inner ring 3. The outer ring 2 is connected to the inner ring 3 by means of, in this case, a total number of six connecting link 4. A connecting link 4 extends mainly perpendicularly from the radial inside face of the outer ring in an angle of 180° perpendicularly in on the radial outside face of the inner ring. The two rings are at a radial distance from each other arranged concentrically about their joint axis.

The connecting links 4 are located at equal angular distance from each other and form a total number of six openings 5 between the outer ring 2 and the inner ring 3. In each opening 5 an elongated mesh 6 is secured for on implantation anchoring the implant 1 in a subjacent fascia (not shown). The mesh 6 is secured around the section 8 of the outer ring 2 that forms part of an opening 5 by means of an anchoring end 7 and is extending to a free end 9 that is fixed to fascia by means of e.g. staples (not shown).

FIGS. 2 and 3 are modifications of the implant in FIG. 1 and like parts are similarly referenced.

In the embodiment 10 in FIG. 2 the mesh 6 is secured in the opening 5 via threads 11 extending from the anchoring end 7 of the mesh 6 to the section 8 of the outer ring 2 that forms part of an opening 5 for distancing the mesh from the inner ring.

FIG. 3 shows a preferred embodiment 12 of an implant according to the invention.

The connecting links 4 connecting the outer ring 2 and the inner ring 3 are in this embodiment so wide that the anchoring part 7 of the mesh 6 can be embedded in at least the section 13 of the outer ring 2 in which a connecting link 4 ends.

The openings 5 are also in this embodiment used for suturing the implant in a hypodermal area, and the meshes 6 are secured to fascia on the way described above.

FIG. 4 shows a fourth embodiment of the present invention, and like parts are similarly referenced.

As the previous embodiments, the fourth embodiment of an implant 14 an inner ring 3 and an outer ring 2. The embodiment of FIG. 4 differs from the others by the fact that both rings 2,3 only have a very small radial and axial extent, the rings preferably being designed as threads interconnected along the outer and inner periphery respectively of the rings via a number of similarly thread-shaped connecting links 4. These connecting links form a number of openings 5 or meshes between the two rings 2,3 so that the two rings appear as a flat, annular mesh from which a number of anchoring means are extending in form of meshes 6. Furthermore the meshes, of which a total number of six are shown in this case, are extending from the inner ring 3 via the outer ring, which is partly incorporated in the mesh 6 towards its free end 9 that serves for being anchored in fascia. Within the scope of the invention implants can be made with any kind of expedient number of anchoring means.

This embodiment is made of a flexible, and optionally more or less elastic, biocompatible material, the many openings or meshes between the rings and in the meshes respectively serving for advantageously receiving a suture or staple when the implant is in its implanted state.

The implant is in this embodiment made with a mainly continuous mesh with identical or different mesh size. This embodiment provides maximum possibility of tissue growing inward without simultaneously preventing the mass movement or peristaltic movement of the intestine.

FIG. 5 shows a fifth embodiment of the present invention, and like parts are similarly referenced.

The fifth embodiment 15 of the implant according to the present invention in FIG. 5 is an alternative to the fourth embodiment in FIG. 4. The inner ring 3 has a larger axial thickness than the outer ring 2 and the connecting links 4 connecting the two rings 2,3 are made of strong thread to thereby distribute loads and stresses equally across the entire extent of the rings.

Preferred radial thicknesses of the rings in the embodiments in FIGS. 1, 2 and 3 are 5 mm, preferably 4 mm, and especially 3 mm.

The thickness of the rings of the embodiments in FIGS. 4 and 5 can be as small as 1 mm and even smaller than 0.5 mm. The axial extent of the rings is typically between 0.5 and 5 mm.

The inside diameter of the inner ring corresponds to or is slightly larger than the outside cross section of the section of intestine which is to be passed through this ring, and the inside diameter of the outer ring is larger than the outside diameter of the inner ring.

Within the scope of the invention it will however be clear to a person skilled in the art that thicknesses and diameters of rings and connecting links depend on the actual need and such that the flexibility and retaining capability are not compromised.

The meshes have an initial length sufficiently great to reach the fascia to which the mesh is to be anchored, the surgeon being able to shorten the mesh to an accurate and sufficient length.

Other types of anchoring means are also comprised within the scope of the invention, for example one single thread can just as well serve to anchor the implant in fascia.

The implant according to the present invention has its preferred application for prophylactic and therapeutic treatment of a hernia originating from an enterostomy.

The implant according to the present invention can however be used in other connections.

For example an implant can be used for surrounding oesophagus to relieve an oesophagus hernia or preventing such a hernia from developing in a previously identified critical site.

The invention claimed is:

1. An implant for implantation into an animal or a human body for preventing herniation, comprising an outer ring, an inner ring that is arranged in the outer ring about a joint axis, and a number of connecting links extending between the outer ring and the inner ring, wherein the inner ring has an outside diameter and the outer ring has an inside diameter that is larger than the outside diameter of the inner ring, wherein a connecting link comprises or at least one thread.

2. The implant according to claim 1, wherein the connecting links are distributed at a mutual angular distance along a ring and jointly forming a number of openings between the inner ring and the outer ring.

3. The implant according to claim 1, wherein the inner ring has a larger axial thickness than the outer ring.

4. The implant according to claim 1, made of a biocompatible material.

5. The implant according to claim 1, wherein the rings each have a radial extent that is smaller than 5 mm.

6. The implant according to claim 5, wherein the radial extent of the rings is smaller than 4 mm.

7. The implant according to claim 5, wherein the radial extent of the rings is smaller than 3 mm.

8. A method for prophylactic or therapeutic treatment of a hernia at a stomy which comprises introducing the implant according to claim 1 on hypodermal implantation in an animal or a human body.

9. The method of claim 8 wherein the implant is applied to the intestine of the animal or human.

10. The implant of claim 1, which is flat in the operative position.

11. The implant of claim 1, wherein the inner and outer rings are located in the same plane.

12. An implant for implantation into an animal or a human body for preventing herniation, comprising an outer ring, an inner ring that is arranged in the outer ring about a joint axis, and a number of connecting links extending between the outer ring and the inner ring, wherein the inner ring has an outside diameter and the outer ring has an inside diameter that is larger than the outside diameter of the inner ring, and at least one elongated anchoring means secured in at least one opening at an anchoring end and extending outwards from the at least one opening to a free end.

13. The implant according to claim 12, wherein an anchoring means is embedded in the outer ring or in at least one anchoring link or in both the outer ring and the at least one anchoring link.

14. The implant according to claim 12, wherein a connecting link comprises at least one rod or at least one thread.

15. An implant for implantation into an animal or a human body for preventing herniation, comprising an outer ring, an inner ring that is arranged in the outer ring about a joint axis, and a number of connecting links extending between the outer ring and the inner ring, wherein the inner ring has an outside diameter and the outer ring has an inside diameter that is larger than the outside diameter of the inner ring, and wherein an anchoring means is secured in an opening via at least one thread extending out from the anchoring end of the anchoring means.

16. An implant for implantation into an animal or a human body for preventing herniation, comprising an outer ring, an inner ring that is arranged in the outer ring about a joint axis, and a number of connecting links extending between the outer ring and the inner ring, wherein the inner ring has an outside diameter and the outer ring has an inside diameter that is larger than the outside diameter of the inner ring, and at least one elongated anchoring means partly extending between two adjacent openings and partly extending outwards from the inner ring via the outer ring to a free end, the section of the outer ring extending between the two openings being integrated in an anchoring means.

17. The implant according to claim 16, which forms a total flexible mesh.

* * * * *

UNITED STATES PATENT AND TRADEMARK OFFICE
CERTIFICATE OF CORRECTION

PATENT NO. : 7,413,569 B2  Page 1 of 1
APPLICATION NO. : 10/537713
DATED : August 19, 2008
INVENTOR(S) : Søgaard-Andersen It is certified that error appears in the above-identified patent and that said Letters Patent is hereby corrected as shown below:

Title Page:
Item (86) PCT No., change "PCT/IL03/02889" to -- PCT/IB03/02889 --.

Column 5:
Line 3 (claim 1, last line), before "at least one thread", delete "or".

Column 6:
Line 2 (claim 12, line 9), before "at an anchoring end", insert -- of the outer ring --.
Line 5 (claim 13, line 2), before "embedded", insert -- anchored to the outer ring by being --;
before "in the", insert -- directly --; before "outer ring", insert -- opening of the --; and before "at least one", delete "in" and insert -- by being attached to --.
Line 6 (claim 13, line 3), delete "or in both the outer ring and the at least one" and insert -- associated with the outer ring --.
Line 7 (claim 13, line 4), delete "anchoring link".
    Claim 13 will then correctly appear as follows:
        13. The implant according to claim 12, wherein an anchoring means is anchored to the outer ring by being embedded directly in the opening of the outer ring or by being attached to at least one anchoring link associated with the outer ring.
Line 17 (claim 17, line 8), before "via at least one", insert -- of the outer ring --.

Signed and Sealed this

Twenty-fourth Day of November, 2009

David J. Kappos
*Director of the United States Patent and Trademark Office*